United States Patent [19]

Fürst et al.

[11] 4,026,921
[45] May 31, 1977

[54] D-HOMOSTEROIDS

[76] Inventors: Andor Fürst, 14 Magnolienpark, Basel; Marcel Müller, 10 Quellenweg, Frenkendorf; Leo Alig, 76 Heidenlochstrasse, Liestal; Peter Keller, 10 Bahnhofstrasse, Therwil, all of Switzerland; Ulrich Kerb, 8 Waitzstrasse; Rudolf Wiechert, 8a Petzowerstrasse, both of Berlin, Germany; Klaus Kieslich, 4 Strasse zum Lowen, Berlin 39, Germany; Karl Petzoldt, 10 Flachsweg, Berlin 38, Germany

[22] Filed: Sept. 20, 1974

[21] Appl. No.: 507,883

[30] Foreign Application Priority Data

Sept. 26, 1973 Germany .................. 2349022

[52] U.S. Cl. .................... 260/488 B; 195/515; 424/311; 424/312; 195/51 A; 424/313; 424/321; 260/293.56; 260/295.5 P; 260/340.5; 260/340.7; 260/340.9; 260/348 A; 260/408; 260/410; 260/456 R; 260/457; 260/468 R; 260/476 C; 260/482 R; 260/484 R; 260/484 B; 260/485 F; 260/485 G; 260/485 H; 260/486 H; 260/486 R; 260/487; 260/586 E; 260/946; 424/214; 424/265; 424/267; 424/278; 424/303; 424/305; 424/308

[51] Int. Cl.² ........................ C07J 63/00

[58] Field of Search .......... 260/488 B, 408, 410 L, 260/586 E, 457, 468 R, 476 C, 946, 485 F, 485 G, 485 H, 486 H, 486 R

[56] References Cited

UNITED STATES PATENTS

| 2,822,381 | 2/1958 | Dodson et al. | 260/488 B |
| 2,860,158 | 11/1958 | Clinton | 260/488 B |
| 3,076,023 | 1/1963 | Kaspar et al. | 260/586 E |
| 3,492,338 | 1/1970 | Hader et al. | 260/488 B |
| 3,939,193 | 2/1976 | Alig et al. | 260/586 E |

OTHER PUBLICATIONS

Chem. Abstracts, 80:37392g.
Chem. Abstracts, 49:6299d.
Chem. Abstracts, 52:11980a.

Primary Examiner—Vivian Garner
Attorney, Agent, or Firm—Samuel L. Welt; George M. Gould

[57] ABSTRACT

Novel D-homosteroids of the formula

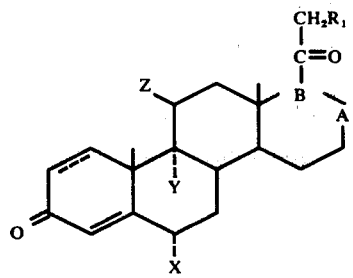

are disclosed. These compounds exhibit anti-inflammatory activity.

31 Claims, No Drawings

D-HOMOSTEROIDS

DESCRIPTION OF THE INVENTION

The present invention relates to new D-homosteroids of the following formula

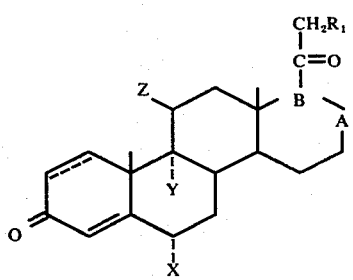

Wherein the designation — — — is a single or double bond in the 1,2-position, X is hydrogen, fluoro or methyl, Y is hydrogen or fluoro when Z is hydroxy or Y is chloro when Z is hydroxy, fluoro or chloro, $R_1$ is hydrogen, fluoro, chloro or free or esterified hydroxy and

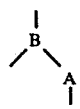

is one of the groups

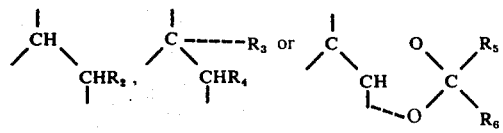

in which $R_2$ is hydrogen or methyl, $R_3$ is hydroxy or acyloxy, $R_4$ is methyl, hydroxy or acyloxy, $R_5$ is hydrogen or lower alky and $R_6$ is lower alkyl or phenyl.

As ester groups which may be utilized in conjunction with the 21-hydroxy substituent $R_1$ one can employ ester functions which are conventionally employed in steroid chemistry such as for example acyloxy groups having from 1 to 16 carbon atoms, sulfate radicals or phosphate radicals. Particularly preferred acyloxy groups are those obtained from straight or branched chain, saturated or unsaturated aliphatic mono or dicarboxylic acids which may in a conventional manner be further substituted with hydroxy, amino or halo.

In addition suitable acyloxy groups may be obtained utilizing cycloaliphatic, aromatic, mixed aromatic-aliphatic or heterocyclic acids which may be further substituted in a manner known per se. Examples of suitable acyloxy groups useful herein include formyloxy, acetoxy, propionyloxy, butyryloxy, pentanoyloxy, hexanoyloxy, octanoyloxy, undecanoyloxy, dimethylacetoxy, trimethylacetoxy, diethylacetoxy, tert.-butylacetoxy, benzoyloxy, phenacetyloxy, cyclopentylpropionyloxy, hydroxyacetoxy, monochloracetoxy, dichloracetoxy, trichloracetoxy, dimethylaminoacetoxy, trimethylaminoacetoxy, diethylaminoacetoxy, piperidinoacetoxy, nicotinoyloxy, ω-carboxypropionyloxy, ω-carboxy-pentanoyloxy and the like.

To prepare water soluble compounds the 21-acyloxy derivatives are employed having a basic nitrogen group in the acyl substituent and such compounds are converted to their corresponding acid addition salt such as for example the hydrochloride, hydrobromide, sulfate, phosphate, oxalate, tartrate or maleate. In addition it is possible to utilize the 21-dicarboxylic acid mono esters such as the sulfuric acid or phosphoric acid esters to obtain an elevated water solubility by converting them into their alkali salts such as for example the sodium or potassium salts.

Suitable ester substituents for the 17-or 17a-position hydroxy group bearing substituent $R_3$ or $R_4$ respectively include acyloxy groups which contain preferably 1 to 8 carbon atoms. Especially preferred acyloxy groups for this purpose include the alkanoyloxy groups such as for example, acetoxy, propionyloxy, butyryloxy, pentanoyloxy or hexanoyloxy.

For those D-homo-steroids of formula I where $R_5$ or $R_6$ are lower alkyl it is to be understood that such groups will preferably include alkyls having from 1 to 4 carbon atoms such as, for example, methyl, ethyl, propyl and butyl.

The novel D-homo-steroids of the present invention are conveniently prepared by a number of alternate process routes.

Thus, for example, one may utilize as starting material a compound of the formula

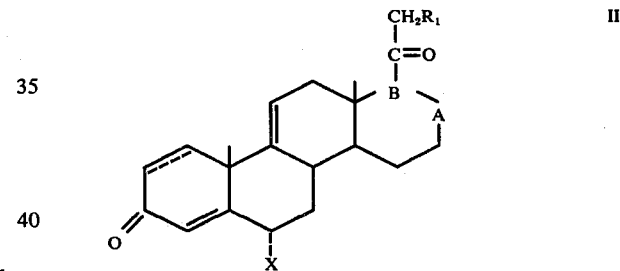

wherein — X, A—B< and $R_1$ are as above and adding to the 9(11)-double bond hypochlorous or hypobromous acid, chlorine, or fluorine and chlorine. The so-obtained 11β-hydroxy 9α-halosteroid may be treated with base to yield the corresponding 9β,11β-epoxysteroid. The latter compound may be submitted to cleavage of the epoxide ring with hydrogen fluoride or hydrogen chloride. If desired, a bromine substituent in the 9α-position can be reductively eliminated.

A starting material of the formula

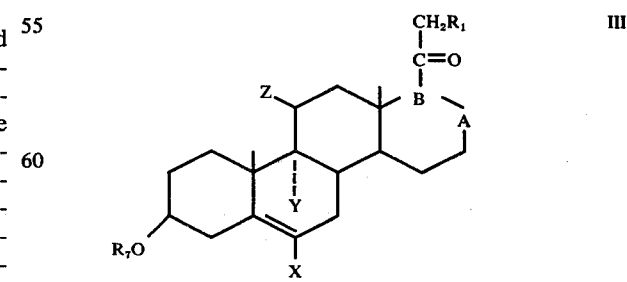

wherein X, Y, Z, —A—B< and $R_1$ are as above and $R_7$ is hydrogen or $C_1$-$C_8$ acyl can be converted to the corresponding 3-keto-$\Delta^4$-steroid by oxidation in a conventional manner, if required, with preliminary saponification of the 3-acyloxy group.

In a further aspect a compound of the formula

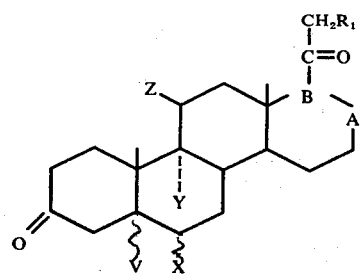

wherein X, Y, Z, —A—B< and $R_1$ are as above and V is hydroxy or bromo can be treated in a manner known per se so as to eliminate HV.

D-homosteroids of the formula I wherein X is hydrogen can be prepared by starting with a compound of the formula

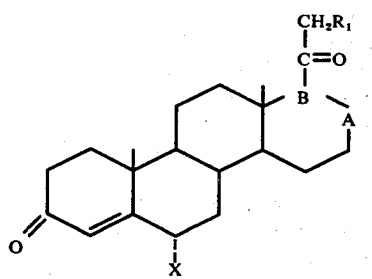

wherein X, —A—B< and $R_1$ are as above and treating such compound with 11β-hydroxylating microorganisms so as to introduce a hydroxy in the 11-position.

Additionally, one may employ as starting material a compound of the formula

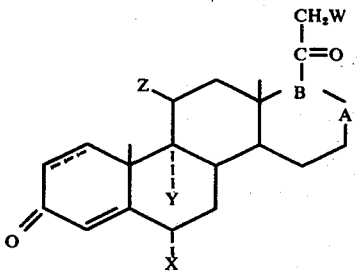

wherein — — —, X, Y, Z and —A—B< are as above and W is alkylsulfonyloxy, arylsulfonyloxy, bromo or iodo. Replacement of the W group in a compound of formula VI by hydrogen, fluoro, chloro, acyloxy or phosphate can be accomplished in a manner known per se.

In order to prepare compounds of formula I wherein $R_3$ and $R_4$ are hydroxy, hydroxy groups may be introduced at positions 17 and 17a of a compound of the formula

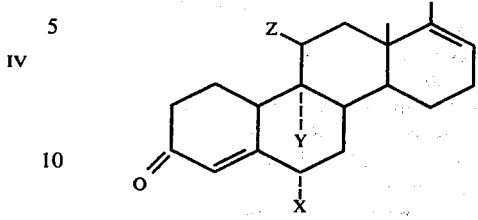

wherein X, Y, Z and $R_1$ are as above.

This introduction of the hydroxy groups may be effected in a manner known per se. Furthermore it is possible to prepare 17-methyl-D-homo-steroids of the present invention by treatment of compounds of the formula

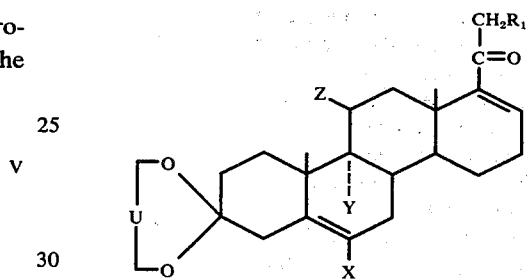

wherein X, Y, Z and $R_1$ are as above and U is an alkylene group, preferably a straight chain alkylene group having from 3 to 10 carbon atoms, most preferably a 2,2-propylene group or a phenyl group with methyl magnesium halide or lithium dimethyl copper. If desired the 20-oxo group can be converted into the 20 enol acylate by reaction with an acyl chloride or acyl bromide and thereafter epoxidized with a peracid and then hydrolyzed by treating the resulting reaction products with an acidic medium.

If desired a D-homo-Δ⁴-steroid produced by the above various process aspects can be dehydrated in the 1-position and/or an existing ester group or ketal group hydrolytically removed and/or an existing hydroxy group esterified or condensed with a carbonyl compound of the general formula $R_5R_6CO$ wherein $R_5$ and $R_6$ are as above.

By utilizing the above various process aspects in a manner known per se it is possible to obtain the following anti-inflammatory active D-homosteroids:
11β,21-dihydroxy-D-homo-4-pregnen-3,20-dione,
11β,21-dihydroxy-D-homo-1,4-pregnadien-3,20-dione.
6α-fluoro-11β,21-dihydroxy-17α-methyl-D-homo-4-pregnen-3,20-dione,
6α-fluoro-11β,21-dihydroxy-17α-methyl-D-homo-1,4-pregnadien-3,20-dione,
9α-fluoro-11β,21-dihydroxy-17α-methyl-D-homo-4-pregnen-3,20-dione
9α-fluoro-11β,21-dihydroxy-17α-methyl-D-homo-1,4-pregnadien-3,20-dione,
6α,9α-difluoro-11β,21-dihydroxy-17α-methyl-D-homo-4-pregnen-3,20-dione, 6α,9α-difluoro-11β21-dihydroxy-17α-methyl-D-homo-1,4-pregnadien-3,20-dione,
6α-fluoro-9α-chloro11β,21-dihydroxy-17α-methyl-D-homo-4-pregnen-3,20-dione,
6α-fluoro-9α-chloro-11β,21-dihydroxy-17α-methyl-D-homo-1,4-pregnadien-3,20-dione,
6α,11β-difluoro-9α-chlor-21-hydroxy-17α-methyl-D-homo-1,4-pregnadien-3,20-dione,
6α-fluoro-9α,11β-dichloro-21-hydroxy-17α-methyl-D-homo-1,4-pregnadien-3,20-dione,
11β,21-dihydroxy-6α,17α-dimethyl-D-homo-4-pregnen-3,20-dione,
11β,21-dihydroxy-6α,17α-dimethyl-D-homo-1,4-pregnadien-3,20-dione,
9α-fluoro-11β,21-dihydroxy-6α,17α-dimethyl-D-homo-1,4-pregnadien-3,20-dione,
9α-chloro-11β,21-dihydroxy-6α,17α-dimethyl-D-homo-1,4-pregnadien-3,20-dione,
as well as the 21-acetate, 21-propionate, 21-butyrate, 21-valerianate, 21-capronate and the sodium salt of the 21-monosulfate ester or 21-monophosphate ester of these compounds, further,
11β,17aα-21-trihydroxy-17α-methyl-D-homo-4-pregnen-3,20-dione,
11β,17aα-trihydroxy-17α-methyl-D-homo-1,4-pregnadien-3,20-dione,
6α-fluoro-11β,17aα,21-trihydroxy-17α-methyl-D-homo-4-pregnen-3,20-dione,
6α-fluoro-11β,17aα,21-trihydroxy-17α-methyl-D-homo-1,4-pregnadien-3,20-dione,
6α,9α-difluoro-11β,17aα,21-trihydroxy-17α-methyl-D-homo-1,4-pregnadien-3,20-dione,
6α,fluoro-9α-chloro-11β,17aα,21-trihydroxy-17α-methyl-D-homo-1,4-pregnadien-3,20-dione,
6α-fluoro-9α,11β-dichloro-17aα,21-dihydroxy-17α-methyl-D-homo-1,4-pregnadien-3,20-dione,
9α-fluoro-11β,17aα,21-trihydroxy-D-homo-4-3,20-dione,
9α-fluoro-11β,17aα,21-trihydroxy-D-homo-1,4-pregnadien-3,20-dione,
11β,17aα,21-trihydroxy-6α,17α-dimethyl-1,4-pregnadien-3,20-dione, as well as,
17a-acetate, 21-acetate, 17a,21-diacetate, 21- butyrate, 21-valerianate, 21-capronate and the sodium salts of the 21-monosulfate ester or these compounds, further,
11β,17α,17aα,21-tetrahydroxy-D-homo-4-pregnen-3,20-dione,
11β,17aα,21-trihydroxy-17α-acetoxy-D-homo-4-pregnen-3,20-dione,
11β,21-dihydroxy-17α,17aα-isopropylidenedioxy-D-homo-4-pregnen-3,20-dione,
11β,17β,17aα,21-tetrahydroxy-D-homo-1,4-pregnadien-3,20-dione,
11β,17aα,21-trihydroxy-17α-acetoxy-D-homo-1,4-pregnadien-3,20-dione,
11β,21-dihydroxy-17α,17aα-isopropylidenedioxy-D-homo-1,4-pregnadien-3,20-dione,
6α-fluoro-11β,17α,17aα,21-tetrahydroxy-D-homo-4-pregnen-3,20-dione,
6α-fluoro-11β,17aα,21-trihydroxy-17α-acetoxy-D-homo-4-pregnen-3,20-dione,
6α-fluoro-11β,21-dihydroxy-17α,17aα-isopropylidenedioxy-D-homo-4-pregnen-3,20-dione,
6α-fluoro-11β,17α,17aα,21-tetrahydroxy-D-homo-1,4-pregnadien-3,20-dione,
6α-fluoro-11β,17aα,21-trihydroxy-17α-acetoxy-D-homo-1,4-pregnadien-3,20-dione,
6α-fluoro-11β,21-dihydroxy-17α,17aα-diacetoxy-D-homo-1,4-pregnadien-3,20-dione,
6α-fluoro-11β,21-dihydroxy-17α,17aα-isopropylidenedioxy-D-homo-1,4-pregnadien-3,20-dione,
6α-fluoro-11β,21-dihydroxy-17α,17aα-(α-phenylethylidenedioxy)-D-homo-1,4-pregnadien-3,20-dione,
6α,9α-difluoro-11β,17α,17aα,21-tetrahydroxy-D-homo-1,4-pregnadien-3,20-dione,
6α,9α-difluoro-11β,21-dihydroxy-17α,17aα-isopropylidenedioxy-D-homo-1,4-pregnadien-3,20-dione,
6α-fluoro-9α-chlor-11β,17α,17aα,21-tetrahydroxy-D-homo-1,4-pregnadien-3,20-dione,
6α-fluoro-9α-chloro-11β,21-dihydroxy-17α,17aα-isopropylidenedioxy-D-homo-1,4-pregnadien-3,20-dione,
6α-fluoro-9α,11β,dichloro-17α,17aα,21-trihydroxy-D-homo-1,4-pregnadien-3,20-dione,
6α-fluoro-9α,11β-dichloro-17α,17aα-isopropylidenedioxy-D-homo-1,4-pregnadien-3,20-dione,
9α-fluoro-11β,17α,17aα,21-tetrahydroxy-D-homo-4-pregnen-3,20-dione,
9α-fluoro-11β,21-dihydroxy-17α,17aα,isopropylidenedioxy-D-homo-4-pregnen-3,20-dione,
9α-fluoro-11β,17α,17aα,21-tetrahydroxy-D-homo-1,4-pregnadiene-3,20-dione, and
9α-fluoro-11β,21-dihydroxy-17α,17aα-isopropylidenedioxy-D-homo-1,4-pregnadiene-3,20-dione,
as well as the 21-acetate, 21-acetate, 21-butyrate, 21-valerianate, 21-capronate and the sodium salts of 21-monosulfate ester or monophosphate ester of these compounds, and further,
21-fluoro-11β-hydroxy-D-homo-4-pregnen-3,20-dione,
21-fluoro-11β-hydroxy-D-homo-1,4-pregnadien-3,20-dione,
21-chloro-11β,-hydroxy-D-homo-1,4-pregnadiene-3,20-dione,
9α,21-difluoro-11β-hydroxy-D-homo-1,4-pregnadiene-3,20-dione,
6α,21-difluoro-11β-hydroxy-17α-methyl-D-homo-1,4-pregnadien-3,20-dione,
6α-fluoro-21-chloro-11β-hydroxy-17α-methyl-D-homo-1,4-pregnadien-3,20-dione,
6α,9α,21-trifluoro-11β-hydroxy-17α-methyl-D-homo-1,4-pregnadien-3,20-dione,
6α,21-difluoro-9α-chloro-11β-hydroxy-17α-methyl-D-hompo-1,4-pregnadien-3,20-dione,
9α,21-difluoro-11β,17aα-dihydroxy-17α-methyl-D-homo-1,4-pregnadien-3,20-dione,
9α,-fluoro-21-chloro-11β,17aα-dihydroxy-17α-methyl-D-homo-1,4-pregnadien-3,20-dione,
6α,21-difluoro-11β,17aα-dihydroxy-17α-methyl-D-homo-1,4-pregnadien-3,20-dione,
6α-fluoro-21-chloro-11β,17aα-dihydroxy-17α-methyl-D-homo-1,4-pregnadien-3,20-dione,
9α,21-difluoro-11β-hydroxy-17α,17aα-isopropylidenedioxy-D-homo-1,4-pregnadien-3,20-dione,
9α-fluoro-21-chloro-11β-hydroxy-17a,17aα-isopropylidenedioxy-D-homo-1,4-pregnadiene-3,20-dione,
6α,21-difluoro-11β-hydroxy-17α,17aα-isopropylidenedioxy-D-homo-1,4-pregnadien-3,20-dione,
6α-fluoro-21-chloro-11β-hydroxy-17α,17aα-isopropylidenedioxy-D-homo-1,4-pregnadien-3,20-dione,
6α,9α,21-trifluoro-11β-hydroxy-17α,17aα-isopopylidenedioxy-D-homo-1,4-pregnadien-3,20-dione,
6α-fluoro-11β,17α,17aα-trihydroxy-D-homo-1,4-pregnadien-3,20-dione, 6α-fluoro-11β-hydroxy-17α,17aα-isopropylidene-dioxy-D-homo-1,4-pregnadien-3,20-dione, and 6α-fluoro-11β,17aα-dihydroxy-17α-methyl-D-homo-1,4-pregnadien-3,20-dione.

It is thus apparent that it is possible to prepare the new D-homo-steriods of the general formula by utilizing processes well known in the art. Thus when employing the process aspect utilizing compounds of formula II as starting materials it is possible to follow various procedures known per se. For example, chlorine by itself or chloro mono fluoride may be added to the $\Delta^{9(11)}$-double bond. A particularly preferred method of adding chlorine and fluorine to the $\Delta^{9(11)}$-double bond involves the use of an N-chloro-acyl amide, such as N-chloro-acetamide or an N-chloroacylimide such as for example N-chlorosuccinimide and hydrogen chloride or hydrogen fluoride or an alkali fluoride or alkali chloride, such as for example, lithium chloride or potassium hydrogen difluoride. The addition of hypochlorous or hypobromous acid to the $\Delta^{9(11)}$ double bond of compounds of formula II can be accomplished utilizing procedures known per se. In particular such reaction is conducted in the presence of water and a mineral acid such as for example sulfuric acid or perchloric acid, a N-chloroacyl amide, N-chloroacylamide, N-bromoacylamide or N-bromo-acylimide such as for example N-chloro-acetamide, N-bromo-acetamide, N-chlorosuccinimide, or N-bromosuccinimide.

In order to prepare the 9α-chloro or fluoro compounds of formula I by the process aspect employing compounds of formula II, one can employ the 11β-hyroxy-9α-bromo compound or in the case of the 9α-fluoro product also the 11β-hydroxy-9α-chloro starting material. In such procedure hypobromous or hypochlorous acid is added to the compound of formula II and the product is then treated with a base such as for example, sodium hydroxide, potassium hydroxide, sodium acetate or potassium acetate and pyridine so as to produce the corresponding 9β,11β-epoxide. This compound is then converted into the 9α-fluoro or 9α-chloro-D-homo-steroid of formula I by treatment with hydrogen chloride in a known manner.

When it is desired to obtain the compounds of formula I which is unsubstituted in the 9α-position, one would convert the compound of formula II into the 11β-hydroxy--9α-bromo derivative as above and then would remove the 9α-bromo atom in a manner known per se. Such removal can be conducted with the help of procedures that are already well known for the reductive debrominations of bromohydrins. It is possible to obtain elimination of bromide utilizing triphenyl tin hydride or tri-m-butyl tinhydride under conditions known in the art.

The process aspect utilizing compounds of formula II as starting materials can employ microbiological, as well as classical procedures. Thus a compound of formula III which contains hydrogen as substituent $R_7$ or lower acyl group with 1 to 6 carbon atoms may be treated with a microorganism of the genus Flavobacterium such as for example, Flavobacterium dehydrogenans, Flavobacterium buccalis or Flavobacterium fulvum in a conventional fermentation procedure thereby producing the corresponding 3-keto-$\Delta^4$-steroids of formula I which are saturated in the 1-position. Under these conditions the acyloxy groups in the 3-position and sometimes in the 21-position are saponified during the conversion.

It is also possible to utilize instead of the microorganisms of the genus Flavobacterium for the aforesaid microbiological oxidation other types of microorganisms, such as for example, strains of the genus Micrococcus such as for example, Micrococcus dehydrogenans, Corynebacterium, such as for example Cornebacterium mediolanum, Norcordia or Fusarium, such as for example, Fusarium solani which can accomplish not only the oxidation of the 3-hydroxy group and the isomerization of the $\Delta^5$ double bond but also the introduction of $\Delta^1$ unsaturation.

The above microbiological operations are preferably conducted on compounds of formula III in which substituent X is hydrogen.

When utilizing classical chemical methods to affect the oxidation of compounds of III, it is necessary that where the 3-position contains an acyl group it is cleaved off in known manner prior to the oxidation. Furthermore it is also desired that in the case wherein the 17α- or 21-position contains a hydroxy group that such function be protected through acylation.

The chemical oxidation of compounds of the general formula III can be carried out utilizing known processes such as for example, by use of Oppenauer oxidation of these compounds utilizing aluminum isopropylate or aluminum tert. butylate in a ketone solvent such as acetone or preferably cyclohexanone.

The conversion of compounds of formula IV can also be carried out in known manner. Thus, for example such compounds can be treated with base such as for example triethylamine, potassium carbonate, calcium carbonate, sodium acetate and lithium carbonate so as to eliminate hydrogen bromide. In addition one may also employ for the elimination of hydrogen bromide or water an inorganic or organic acid such as for example formic acid, acetic acid, oxalic acid, hydrochloric acid, phosphoric acid and sulfuric acid. Use of this latter procedure for elimination will cause isomerization if there is a substituent X (fluoro or methyl in the β-position).

The conversion of compounds of formula V can be carried out by utilizing known fermentation procedures with 11β-hydroxylating microorganisms. Suitable organisms for this purpose include fungus strains of the genus Curvularia, for example, *Curvularia lunata, Cunninghamella*, for example, *Cunninghamella bainieri, Cunninghamella elegans, Cunninghamella echinolata* and *Cunninghamella blakesleeana*, Absidia, for example *Absidia orchidis* and *Absidia coerula*, Helminthosporium, Rhizoctonia, for example, *Rhizoctonia solani*, Verticillium for example, *Verticillium theobromae, Stachylidium*, for example *Stachylidium* bicolor, Pellicularia, for example, *Pellicularia filamentosa* or Collectotrichum, for example *Colletotrichum pisi*. Such fermentation with such organisms can be carried out under known conditions. Under such treatment any acyl group in the 21-position will usually be cleaved. This process aspect is preferably carried out with compounds of formula V which bear a hydroxy or an acyloxy group in the 21-position.

The processes employing starting materials of formula VI are those which are generally utilized to exchange in an organic compound a bromo, iodo, alkanesulfonyl, preferably methanesulfonyl or arylsulfonyl, preferably p-toluenesulfonyl substituent by hydrogen, fluoro, chloro, acyloxy or phosphate. Thus for example one can treat compounds of the general formula VI wherein W is iodo or a p-toluenesulfonyl group with zinc dust so as to eliminate the aforesaid substituents and thus obtain the corresponding 11-unsubstituted D-homo-steroid of formula I. Further, one can react the compounds of formula VI in a polar solvent with an alkali halide, preferably potassium hydrogen difluoride or lithium chloride or with an alkali acylate such as for example sodium acetate thereby obtaining the corresponding 21-fluoro, 21-chloro or 21-acyloxy compounds of formula I. For this reaction one preferably employs as a polar solvent a dipolar aprotic solvent such as dimethylformamide, dimethyl acetamide, hexamethylphosphoric acid triamide or N-methyl pyrrolidone which one may combine as desired with a smaller amount of protonic solvent, such as methanol, ethanol or water. When one conducts this process aspect utilizing an alkali acylate as a reaction partner, then it is necessary that the solvent for the reaction is the corresponding free carboxylic acid. The 21-bromo or 21-iodo compounds of formula VI can be converted into the corresponding 21-fluoro or 21-acyloxy compounds by treatment with silver fluoride or silver acylate such as, for example, silver acetate. The 21-monophosphate ester of formula I can be readily prepared by heating the corresponding iodo compound of formula VI with phosphoric acid in the presence of an organic base such as triethylamine. The process employing compounds of formula VII as starting materials can be carried out in known manner utilizing techniques generally employed for converting a $\Delta^{16}$-steroid into a 16,17-dihydroxy steroid. Thus, for example, one such procedure would involve treating a compound of formula VII with osmium tetraoxide or with potassium permanganate.

Similarly, the conversion of compounds of VIII follows procedures well known in the art wherein methyl addition to a $\Delta^{16}$-double bond of pregnan-20-one derivative is carried out. Thus one can for example react a compound of formula VIII with a methyl magnesium halide, preferably in the presence of cuprous chloride or with lithium dimethyl copper and thereafter work up the Grignard solution in known manner, e.g., with mineral acid to thereby obtain a D-homo-steroid of formula I containing a 17α-methyl and a 17aα-hydrogen. If one were to treat the above Grignard solution with an acyl halide such as acetyl chloride, epoxidize the reaction mixture by treatment with peracid and thereafter treat the reaction mixture with mineral acid, one obtains a compound of formula I substituted with a 17α-methyl and a 17aα-hydroxy.

Working up of the reaction mixture utilizing an acid medium results in cleavage of a ketal group in the 3-position and simultaneously isomerizing the $\Delta^5$-double bond. Dehydration in the 1-position in a $\Delta^4$-D-homo-steroid of formula I saturated in the 1-position can be conveniently carried out utilizing known biological techniques as well as by employing classical chemical methods. Thus one can treat a $\Delta^4$-steroid in a known manner with a bacterial culture of the genus Bacillus such as for example, Bacillus lentus or Bacillus sphaericus or Arthrobacter, such as for example, Arthrobacter simplex so as to dehydrate in the 1-position. Alternatively, it is also possible to effectuate the $\Delta^1$ dehydration utilizing techniques conventional in steroid chemistry for treating a $\Delta^4$-steroid with known oxidation agents such as for example, with selenium dioxide or 2,3-dichloro-5,6-dicayno benzoquinone in an inert solvent with heating.

The above mentioned saponification of 17,17a- and-/or 21-positioned acyloxy group can be carried out in a known manner such as for example by treating the ester in an aqueous or alcoholic solvent in the presence of a strong acid such as for example, sulfonic acid, hydrochloric acid, p-toluenesulfonic acid or trifluoroacetic acid or by the treatment of said ester in aqueous or alcoholic solvents or solvent mixtures in the presence of an alkali alcoholate, alkali hydroxide or alkali carbonate.

When the saponification is carried out under mild conditions it is possible to selectively saponify a 17aα-21-diacyloxy-D-homo-steroid of formula I to the corresponding 21-hydroxy-17aα-acyloxy-D-homo-steroid.

If desired a ketal group in the 17,17a-position can be hydrolyzed. This can be accomplished by treating such compounds with acid in an aqueous solvent or an aqueous solvent mixture.

The esterification of free hydroxyl groups in the 17,17a-and/or 21-positions can also be effected following procedures well known in the art. Thus one can, for example, treat the hydroxy steroid with acyl chloride or acyl anhydride in the presence of acid, such as for example, hydrochloric acid, p-toluenesulfonic acid, trifluoroacetic acid or in the presence of a base such as potassium carbonate, pyridine, collidine or p-dimethylamine pyridine. Alternatively, it is possible to esterify the hydroxy compound utilizing a carbonic acid in the presence of trifluoroacetic anhydride. By employing mild conditions for these esterifications it is possible to selectively esterify primary and secondary hydroxyl groups while retaining free tertiary hydroxyl groups. It is also possible to selectively esterify the 21-hydroxyl group of a 17,17a,21-trihydroxy steroid by treating the trihydroxy compound with a corresponding acyl anhydride in the presence of lead acetate.

It is also possible utilizing known procedures to convert a 21-hydroxy compound of formula I into the alkali sulfate of a 21-mono sulfonic acid ester such as for example by treating the 21-hydroxy compound with sulfur trioxide in pyridine and then converting the resulting sulfonic acid ester into its alkali salt by treating with an alkali base.

If desired it is possible to condense a compound of formula I having a 17,17a-diol group with a carbonyl compound of the formula $R_5R_6CO$. This reaction is conveniently carried out by reacting the diol with an excess of the aforesaid carbonyl compound in the presence of strong acid such as for example, hydrochloric acid, perchloric acid or p-toluenesulfonic acid and also in the presence of a water abstracting agent such as for example, an enol acetate of an ortho formic acid trialkyl ester.

The novel D-homo-steroids of formula I are pharmaceutically active substances and are especially valuable in that they exhibit an excellent level of anti-inflammatory activity while at the same time exhibiting only low levels of side reactions. The onset of activity and the duration of activity of these new D-homo-steroids as well as their solubility in physiologically acceptable solvents can be adjusted in the manner well known for croticoids such as for example, selecting specific acids for esterifying the 17,17a and/or 21-hydroxy groups.

The D-homosteroids of formula I exhibit an excellent anti-phlogistic activity and because they show a good disassociation of the aforesaid desirable activity from the undesired thymolytic, catabolic and mineral corticoid side reactions they are of particular usefulness as medicinal agents. As medicinal agents they may be incorporated in a known manner into dragees and capsules which may contain, for example 0.1 – 5 mg. of the D-homo-steroid of the invention and 50 mg. – 2 g. of a pharmacologically inert support material such as for example, lactose, amylose, talcum, gelatin, magnesium stearate and the like as well as combinations of the aforementioned. For topical applications it is possible to incorporate preferably 0.01 to 2% of the D-homo-steroids of the present invention into conventional powder, salve, aerosol and other similar conventional topical formulations.

The starting materials of formulas II to VIII can be prepared in analogy to the procedures presented above and specifically in analogy to the examples provided hereafter.

EXAMPLES

I. Syntheses

EXAMPLE 1

(a) A total of 130 ml of methyl iodide was added dropwise to 45 g magnesium turnings in 1400 ml of absolute ether. After the magnesium has dissolved, 2500 ml of absolute tetrahydrofuran is added slowly and the mixture is distilled until the distillate reaches a boiling point of 55° C. The mixture is then cooled to 20° C, 7 g of cuprous chloride is added and then a solution of 100 g of 3$\beta$-acetoxy-D-homo-pregna-5,17(17a)-dien-20-one and 100 ml of absolute tetrahydrofuran is added and the mixture stirred for 40 minutes at 20° C. Thereafter the mixture is cooled to 0° C., 230 ml. of 2-N-sulfuric acid is added dropwise and the mixture is then extracted with ethyl acetate. The organic extract was washed with sodium thiosulfate and water, dried over sodium sulfate and concentrated in vacuo. The resulting resude was taken up with heating in 300 ml. pyridine and 150 ml. of acetic anhydride and the resulting solution was allowed to stand for 16 hours at room temperature. Then the mixture was thrown into ice water, the precipitated product filtered off and then dissolved in methylene chloride. The methylene chloride solution was washed with dilute sulfuric acid and water, concentrated in vacuo and the residue crystallized from methylene chloride - ethyl acetate. There was thus obtained 75.6 g. of 3$\beta$-acetoxy-17$\alpha$-methyl-D-homo-5-pregnen-20-one melting at 212°–213° C.

b. A total of 30 g. of 3$\beta$-acetoxy-17$\alpha$-methyl-D-homo-5-pregnen-20-one was treated with 300 ml. of glacial acetic acid and heated to 40°–45° C. Then over a period of 10 minutes there was added dropwise a solution of 7.9 ml. of bromine in 60 ml. of glacial acetic acid. Then after the reactionmixture has cooled off it is thrown into ice cold potassium acetate solution, the precipitated product filtered off, taken up in ethyl acetate, the organic phase washed with water, taken to dryness at 40° bath temperature and one obtains as a crude product 5,6,21-tribromo-3$\beta$-acetoxy-17$\alpha$-methyl-D-homo-pregnen-20-one.

c. The resulting tribromo crude product above was treated with 800 ml of acetone and 80 g. of sodium iodide and was stirred for 16 hours at 20° C. in darkness. Thereafter the reaction mixture is treated with ice cold sodium thiosulfate solution, the precipitated iodide if filtered off, dissolved in ethyl acetate, the organic phase washed with water and then taken to dryness in vacuo.

d. The resulting residue is dissolved in 420 ml. of dimethylformamide, treated with 24 ml. of glacial acetic acid and 42 ml. of triethylamine and then stirred for 4½ hours under nitrogen at 110° C. The reaction mixture is allowed to cool to room temperature then thrown into ice cold sodium chloride solution, the precipitated product filtered off and taken up in methylene chloride. The methylene chloride solution is washed with water, dried over sodium sulfate, concentrated in vacuo and the residue is purified chromatographically over a silica gel column. There was thus obtained 19.5 g. of 3$\beta$,21-diacetoxy-17$\alpha$-methyl-D-homo-5-pregnen-20-one which after recrystallization from ether-pentane melts at 135.5°–137.5° C.

e. A total of 24.4 g. of 3$\beta$,21-acetoxy-17$\alpha$-methyl-D-homo-5-pregnen-20-one was dissolved 250 ml. of methylene chloride, treated with 250 ml. of 1% methanolic potassium hydroxide solution and then heated for 25 minutes under reflux. A total of 3 ml. of glacial acetic acid is added to the reaction mixture, it is then conentrated in vacuo, the residue is taken up in tetrahydrofuran and the solution concentrated in vacuo once more. The residue was recrystallized from acetone to yield 15.8 g. of 3$\beta$,21-dihydroxy-17$\alpha$-methyl-D-homo-5-pregnen-20-one melting at 198°–202° C.

f. A total of 11.7 g. of 3$\beta$,21-dihydroxy-17$\alpha$-methyl-D-homo-5-pregnen-20-one was treated with 150 ml. of dimethylformamide, 20 ml. of acetic anhydride and 1.1 g. of lead diacetate and stirred for 90 minutes at room temperature. The mixture was thrown into ice cold sodium chloride solution, the precipitated product filtered off and dissolved in methylene chloride. The methylene chloride extract was washed with water, dried and concentrated in vacuo. The resulting product was recrystallized from methylene chloride and isopropyl ether to yield 11.6 g of 3$\beta$-hydroxy-21-acetoxy-17$\alpha$-methyl-D-homo-5-pregnen-20-one melting at 188.5°–191° C.

g. A total of 20.5 g of 3$\beta$-hydroxy-21-acetoxy-17$\alpha$-methyl-D-homo-5-pregnen-20-one was treated with 500 ml of toluene and 20 ml of cyclohexanone and heated to boiling until several ml of the solvent is distilled off. Then to the mixture is added a solution of 4.4 g of aluminum isopropylate in 50 ml of toluene, with heating of the solution for over an hour so that some of the solvent is continuously distilled off.

The reaction mixture is allowed to cool off, it is diluted with ethyl acetate, the organic phase washed with 1N sulfuric acid and water and taken to dryness in vacuo. The residue was purified by chromatography over a silica gel column and recrystallized from acetone/hexane so as to yield 15.7 g. of 21-acetoxy-17$\alpha$-methyl-D-homo-4-pregnen-3,20-dione melting at 200.5°–202° C.

h. A 2 liter Erlenmeyer flask containing 500 ml. of a nutrient broth comprising 1% corn steep liquor, 1% soy powder and 0.005% soy oil which had been sterilized in an autoclave for 30 minutes at 120° C. and adjusted to a pH of 6.2, was inoculated with a lyophiled culture of Curvularia lunata (NRRL 2380) and shaked for 72 hours at 30° C. on a rotating shaker. This preliminary culture was then used to inoculate 15 l. of growth medium which had been sterilized at 21° C. and 1.1 atmospheres comprising 1% corn steep liquor, 0.5% glucose and 0.005% soy oil, said medium being adjusted to pH 6.1 and contained in a 20 l. fermentor made of stainless steel. The mixture, together with Silicon SH as a defoamer, was allowed to germinate for 24 hours at 29° C.

under aeration (10 l./min.) at 0.7 atmospheres pressure and stirring at 220 rotations per minute. 1 l. of this culture browth was introduced under sterile conditions into 13 l. of sterilized medium comprising 1% corn steep oil, 1.25% soy powder and 0.005% soy oil and then fermented under the same conditions. After 6 hours a solution of 3 g. of 21-acetoxy-17α-methyl-D-homo-4-pregnen-3,20-dione and 150 ml. of dimethylformamide was added. After 23 hours of contact time the fermentation solution was and stirred twice with 10 l. of methyl isobutyl ketone. The extracts were concentrated with a 50° C. bath temperature in vacuo to dryness. The residue was freed of the silicone oil by washing with hexane and then crystallized from ethyl acetate utilizing activated charcoal. There was thus obtained 6.08 mg of pure 11β-21-dihydroxy-17α-methyl-D-homo-4-pregnen-3,20-dione melting at 200.3° C.

EXAMPLE 2

A 2 l. Erlenmeyer flask containing 500 ml. of a growth medium comprising 1.5% of peptone, 1.2% corn steep and 0.2% $MgSO_4$ were sterilized in an autoclave at 120° C. for 30 minutes. The pH is then adjusted to 6.5, the medium inoculated with a lyophiled culture of Bacillus lentus (ATCC 13 805) and then shaken for 24 hours at 30° C. This initial culture was then inoculated into a 20 l. stainless steel fermentor containing 15 l. of a liquid nutrient medium which had been sterilized at 120° C. and at 1.1 atmospheres comprising 0.2% of a yeast extract, 1% corn steep liquor and 0.1% glucose which had been adjusted to pH 7.0. Together with Silicon SH as an antifoam agent it was germinated at 29° C. under aeration and stirring. After a period of 6 hours there was introduced a solution of 3 g. of 11β,21-dihydroxy-17α-methyl-D-homo-4-pregnen-3,20-dione in 150 ml. of dimethylformamide. After 15 hours of contact time the fermentation was stopped, extracted twice with 10 ml. of methylisobutyl ketone and the extracts concentrated in vacuo. The residue was washed free of silicon oil with hexane and recrystallized from acetone/ diisoporpyl ether in the presence of activated carbon so as to yield 2.2 g. of 11β,21-dihydroxy-17α-methyl-D-homo-1,4-pregnadien-3,20-dione melting at 159° C.

EXAMPLE 3

A total of 200 mg. of 11β,21-dihydroxy-17α-methyl-D-homo-1,4-pregnadien-3,20-dione was treated with 3 ml. of pyridine and 0.3 ml. of butyric acid anhydride and then heated for 15 minutes under reflux. The mixture was allowed to cool, it was diluted with cyclohexane and then concentrated to dryness in vacuo. The oily residue was triturated with pentane, the pentane solution decanted off and the resulting crude product recrystallized from methylene chloride-diisopropyl ether. There was thus obtained 140 mg. of 11β-hydroxy-21-butyryloxy-17α-methyl-D-homo-1,4-pregnadien-3,20-dione melting at 156°–158° C.

EXAMPLE 4

A total of 5.0 g. of 11β,21-dihydroxy-17α-methyl-D-homo-1,4-pregnadien-3,20-dione was treated with 20 ml of pyridine and 10 ml of acetic anhydride and was kept for 60 minutes at room temperature. Then the reaction mixture was thrown into ice water, the precipitated product filtered off, dissolved in methylene chloride, the organic phase washed with 2N sulfuric acid and water and taken to dryness in vacuo. The residue was recrystallized from methylene chloride-diisopropyl ether and there was thus obtained 5.1 g of 11β-hydroxy-21-acetoxy-17α-methyl-D-homo-1,4-pregnadien-3,20-dione melting at 170°–172° C.

EXAMPLE 5 a. A total of 50 g. of 11β-hydroxy-21-acetoxy-17α-methyl-D-homo-1,4-pregnadien-3,20-dione was dissolved in 44 ml. of pyridine and with stirring a total of 22 ml. of methane sulfonyl chloride was added dropwise. The reaction mixture was heated for 90 minutes at 80° C., allowed to cool and then thrown into ice water. The precipitated product was filtered off, washed with water, dried in vacuo, recrystallized from melthylene chloride-diisopropyl ether and there was thus obtained 39.2 g. of 21-acetoxy-17α-methyl-D-homo-1,4,9-(11)-pregnatriene-3,20-dione melting at 161°–163° C.

b. A total of 11 g. of 21-acetoxy-17α-methyl-D-homo-1,4,9(11)pregnatrien-3,20-dione was suspended in 200 ml. of tetrahydrofuran and treated with 88 ml. of 1-N-perchloric acid. Then with stirring a total of 14.3 g. of N-bromosuccinimide was added to the reaction mixture and stirring was continued for 30 minutes at 30° C. The mixture was thrown into ice cold sodium sulfite solution, the precipitated product filtered, taken up in methylene chloride, the methylene chloride phase washed with water, concentrated in vacuo and there was thus obtained crude 9α-bromo-11β-hydroxy-21-acetoxy-17α-methyl-D-homo-1,4-pregnadien-3,20-dione.

c. A total of 13.6 g. of the aforesaid bromo compound was treated with 22 g. of potassium acetate and 100 ml. of ethanol and then heated for 2 hours under reflux. The reaction mixture was thrown into water, the precipitated product filtered off, dried in vacuo and there is thus obtained crude 9β,11β-epoxy-21-acetoxy-17α-methyl-D-homo-1,4-pregnadien-3,20-dione.

d. A total of 8.0 g. of the aforesaid epoxide compound was added to a mixture of 24 ml. of dimethyl formamide and 24 ml. of hydrogen fluoride at −10° C. and the mixture was then stirred for 10 hours at room temperature. The mixture was then thrown into ammoniated ice water, the precipitated product filtered off, dissolved in methylene chloride, the methylene chloride phase washed with water and concentrated in vacuo. The residue was recrystallized from acetone-hexane to yield 5.8 g. of 9α-fluoro-11β-hydroxy-21-acetoxy-17α-methyl-D-homo-1,4-pregnadien-3,20-dione melting at 183°–185° C.

EXAMPLE 6

A total of 3 g. of the 9α-fluoro compound of Example 5 was dissolved in 12 ml. of methanol and 12 ml. of methylene chloride, cooled to −5° C. and then treated dropwise with a solution of 0.18 g. of potassium hydroxide. The mixture was stirred for 60 minutes at 0° C., neutralized with acetic acid, diluted with methylene chloride, the methylene chloride phase washed with water, taken to dryness in vacuo and the residue crystallized from methanol. There was obtained 2.4 g. of 9α-fluoro-11β,21-dihydroxy-17α-methyl-D-homo-1,4-pregnadien-3,20-dione melting at 223°–225° C.

EXAMPLE 7

A total of 4 ml. of pyridine was cooled to −15° C. and then treated with stirring with 0.26 ml. of freshly distilled sulfur trioxide in such manner that the internal temperature of the mixture does not exceed +5° C. Into the resulting solution there is added 2 g. of 9α-fluoro-11β,21-dihydroxy-17α-methyl-D-homo-1,4-pregnadien-3,20-dione. The mixture was stirred for 30 minutes at 20° C., treated with 40 ml. of water and then stirred for an additional 30 minutes. The pH of the reaction mixture is then adjusted with about 7 ml. of 1-N sodium hydroxide solution to 8.5. The mixture was extracted with methylene chloride and the aqueous phase thereafter adjusted to a pH of 8.5 with IN sodium hydroxide solution and concentrated in vacuo. The residue was dissolved in 50 ml. of methanol, filtered, the filtrate concentrated in vacuo and the residue dried in vacuo. There was thus obtained 1.8 g. of sodium-[9α-fluoro-11β-hydroxy-3,20-dioxo-17α-methyl-D-homo-1,4-pregnadien-21-yl]-sulfate decomposing at 191° C.

EXAMPLE 8 a. A Grignard solution (prepared from 21 g. of magnesium turnings, 72.5 g. of Me I and 1,000 ml. of ether) was diluted with 1,000 ml. of tetrahydrofuran and distilled for a period until the distillate reaches a boiling point of 50° C. The resulting suspension is cooled to 20° C., treated with 4 g. of cuprous chloride and a solution of 50 g. of 3β-hydroxy-D-homo-5,17(17a)-pregnadien-20-one in 2,000 ml. of absolute tetrahydrofuran. The mixture is stirred for 20 minutes at room temperature. After workup in the usual manner the crude product is crystallized from acetone so as to yield 32.5 g. of 3β-hydroxy-17α-methyl-D-homo-5-pregnen-20-one melting at 207°–209° C.

b. A total of 10 g. of the above 3β-hydroxy compound was suspended in 1,000 ml. of tetrahydrofuran and treated dropwise with a solution of 3.6 ml. of bromine in 10 ml. of glacial acetic acid over a period of about 15 minutes. The reaction mixture is worked up as described in Example 1(b) and there is obtained crude 3β-hydroxy-5,6,21-tribromo-17α-methyl-D-homo-pregnan-20-one.

c. The so obtained tribromo derivative was then treated and worked up in the manner of Example 1(c) above with 300 ml. of acetone and 35 g. of sodium iodide so as to yield the corresponding crude 21-iodo compound.

d. The 21-iodo compound was dissolved in 140 ml dimethyl formamide, treated with 8 ml of glacial acetic acid and 14 ml of triethylamine and then stirred at 90° C for 11 hours. There was obtained after workup in the manner of Example 1(d) 4.4 g of 3β-hydroxy-21-acetoxy-17α-methyl-D-homo-5-pregnen-20-one which after recrystallization from methylene chloride/diisopropyl ether melted at 188°–190° C.

e. In a solution of 3 ml. of hydrogen fluoride and 3 ml. of dimethyl formamide cooled to −30° C., there was added 470 mg. of N-bromo succinimide. To this mixture there was then added portionwise a cooled solution of 1 g. of 3β-hydroxy-21-acetoxy-17α-methyl-D-homo-5-pregnen-20-one in 8 ml. of methylene chloride. The mixture was stirred for 10 minutes at −30° C, thrown into ice cold potassium biocarbonate solution and extracted with methylene chloride. The methylene chloride phase was washed with water, concentrated to dryness in vacuo and the residue recrystallized from acetone to yield 627 mg. of 6β-fluoro-5α-bromo-3β-hydroxy-21-acetoxy-17α-methyl-D-homo-5α-pregnan-20-one melting at 168.5° C. (decomposition).

f. A total of 300 mg. of 6β-fluoro-5α-bromo-3β-hydroxy-21-acetoxy-17α-methyl-D-homo-5α-pregnan-20-one in 10 ml. of acetone was treated dropwise with 0.19 ml. of Jones reagent (containing per liter 267 g. of chromium (VI)-oxide and 230 ml. of concentrated sulfuric acid) and the mixture stirred for 10 minutes at 20° C. Then the mixture was thrown into ice water, the precipitated product filtered off, taken up in methylene chloride, the methylene chloride phase washed with water and then concentrated in vacuo. There was thus obtained 298 mg. of crude 6β-fluoro-5α-bromo-21-acetoxy-17α-methyl-D-homo-5α-pregnan-3,20-dione.

g. The aforesaid crude product was dissolved in 5 ml. of glacial acetic acid and stirred for 3 hours at 30° C. Then the mixture was treated with 100 mg. of sodium acetate, stirred for 10 minutes at 30° C, thrown into ice water, the precipitated product filtered off and taken up into methylene chloride. The methylene chloride phase was washed with water, concentrated in vacuo and the residue recrystallized from acetone to yield 250 mg. of 6α-fluoro-21-acetoxy-17α-methyl-D-homo-4-pregnen-3,20-dione.

h. Utilizing the procedure in Example 1(h) 3 g. of 6α-fluoro-21-acetoxy-17α-methyl-D-homo-4-pregnen-3,20-dione was fermented with Curvularia lunata, worked up and there was thus obtained 6α-fluoro-11β,21-dihydroxy-17α-methyl-D-homo-4-pregnen-3,20-dione.

EXAMPLE 9

In the manner of Example 2, 1.2 g. of 6α-fluoro-11β,21-dihydroxy-17α-methyl-D-homo-4-pregnen-3,20-dione was treated with a culture of Bacillus lentus, worked up and there was thus obtained 6α-fluoro-11β,21-dihydroxy-17α-methyl-D-homo-1,4-pregnadien-3,20-dione.

EXAMPLE 10

A total of 10 g. of the diene product of Example 9 in 40 ml. of pyridine was treated with 20 ml. of acetic anhydride and stirred for 90 minutes at room temperature. After workup of the reaction mixture in the manner described in Example 3 there is obtained 9.5 g. of 6α-fluoro-11β-hydroxy-21-acetoxy-17α-methyl-D-homo-1,4-pregnadiene-3,20-dione melting at 213°–215° C.

EXAMPLE 11 a. A total of 5 g. of 6α-fluoro-11β,21-dihydroxy-17α-methyl-D-homo-1,4-pegnadien-3,20-dione was treated with 15 ml. of pyridine and 5 ml. of trimethyl acetic acid anhydride and then heated at reflux for 6 hours. The reaction mixture was diluted with 30 ml. pyridine, cooled to +5° C., a solution of 2 ml. of thionyl chloride was added dropwise and the mixture stirred for 30 minutes at 0° C. The mixture was then thrown into ice water, the precipitated product collected, washed with water, dried in vacuo and crystallized from methylene chloride so as to yield 4.9 g. of 6α-fluoro-21-trimethylacetoxy-17α-methyl-D-homo-1,4,9(11)-pregnatrien-3,20-dione melting at 191°–192.5° C.

b. A total of 380 mg. of the above teimethylacetoxy derivative was dissolved in 15 ml. of tetrahydrofuran and then treated with 1.2 g. of N-chloro succinimide and 11 ml. of IN aqueous perchloric acid. The mixture was stirred for 3 hours at 35° C, thrown into ice water, extracted with methylene chloride, the methylene chloride phase washed with water and then concentrated in vacuo. The residue was recrystallized from acetone-diisopropyl ether to yield 250 mg. of 6α- fluoro-9α-chloro-11β-hydroxy-21-trimethylacetoxy-17α-methyl-D-homo-1,4-pregnadien-3,20-dione melting at 221°–223° C.

EXAMPLE 12 a. A total of 500 mg. of 6α-fluoro-11-hydroxy-21-acetoxy-17α-methyl-D-homo-1,4-pregnadien-3,20-dione was treated with 25 ml. of diemthylformamide, 4.5 ml. of pyridine and 2.2 ml. of methane sulfonyl chloride and heated for 90 minutes at 80° C. After workup in the manner of Example 5(a) there was obtained 402 mg. of 6α-fluoro-21-acetoxy-17α-methyl-D-homo-1,4,9(11)-pregnatrien-3,20-dione b. A total of 375 mg. of the above triene derivative was dissolved in 15 ml. of tetrahydrofuran and then treated with 1.2 g. of N-chlorosuccinimide and 11 ml. of 1-N-aqueous perchloric acid. The mixture was stirred for 3 hours at 35° C. After workup in the manner of Example 11(b) there was obtained 266 mg. of 6α-fluoro-9α-chloro-11β-hydroxy-21-acetoxy-17α-methyl-D-homo-1,4-pregnadien-3,20-dione melting at 207°–209° C.

EXAMPLE 13 a. In analogy to the procedure of Example 5(a) a total of 5.0 g. of 6α-fluoro-11β-hydroxy-21-acetoxy-17α-methyl-D-homo-1,4-pregnadien-3,20-dione produced 3.7 g. of 6α-fluoro-21-methyl-D-homo-1,4,9(11)-pregnatrien-3,20-dione b. The resulting pregnatriene compound was then converted following the procedure of Examples 5(b) – (d) into 6α,9α-difluoro-11β-hydroxy-21-acetoxy-17α-methyl-D-homo-1,4-pregnadien-3,20-dione melting at 199°–201° C.

EXAMPLE 14

A total of 3.0 g. of the 6α,9α-difluoro compound of Example 13 was treated in the manner of Example 6 so as to produce 2.6 g. of 6α,9α-difluoro-11β,21-dihydroxy-17α-methyl-D-homo-1,4-pregnadien-3,20-dione melting at 190°–191° C.

EXAMPLE 15

A total of 1.0 g. of 6α-fluoro-21-acetoxy-17α-methyl-D-homo-1,4,9(11)-pregnatriene-3,20-dione was dissolved in 50 ml. of glacial acetic acid, treated with 4 g. of lithium chloride and cooled to 0° C. To this mixture there was added 400 mg. of N-chlorosuccinimide and a solution of 110 mg. of hydrogen chloride in 1 ml. of tetrahydrofuran, the mixture is stirred for 5 hours at room temperature and then thrown into ice water. The precipitated product is filtered off, taken up in methylene chloride, the methylene chloride phase washed with water, concentrated in vacuo and the residue crystallized from ether-pentane to yield 590 mg. of 6α-fluoro-9α,11β-dichloro-21-acetoxy-17α-methyl-D-homo-1,4-pregnadien-3,20-dione melting at 232°–234° C.

EXAMPLE 16

A mixture of 4.2 ml. of hydrogen fluoride 5.7 ml. of tetrahydrofuran and 8 ml of methylene chloride was cooled to −70° C., treated with 2.0 g. of 6α-fluoro-21-acetoxy-17α-methyl-1,4,9(11)-pregnatrien-3,20-dione and 1.0 g. of N-chlorosuccinimide and the mixture stirred for 5 hours at −60° C. There was then added to the mixture an additional 2.0 g. of N-chlorosuccinimide and the mixture allowed to stand at 0° C. for 15 hours. The reaction mixture was then added to ice cold potassium bicarbonate solution, extracted with methylene chloride, the methylene chloride phase washed phase washed with sodium sulfate solution and water and concentrated in vacuo. The residue was recrystallized from acetone/hexane to yield 1.3 g. of 6α,11β-difluoro-9α-chloro-21-acetoxy-17α-methyl-D-homo-1,4-pregnadien-3,20-dione melting at 244°–246° C.

EXAMPLE 17

A total of 20 ml. of methane sulfonyl chloride was added dropwise with stirring and cooling to a solution of 20 g. of 6α-fluoro-11β,21-dihydroxy-17α-methyl-D-homo-1,4-pregnadien-3,20-dione in 200 ml. of pyridine. After a reaction period of 30 minutes the solution was thrown into ice water and the precipitated 21-mesylate filtered off. The resulting 15.4 g. of 6αfluoro-11β-hydroxy-21-mesyloxy-17β-methyl-D-homo-1,4-pregnadien-3,20-dione was dissolved in 500 ml. of acetone and then together with 15.4 g. of sodium iodide in 400 ml. of acetone was heated to boiling for 15 minutes. The filtered reaction solution was concentrated in vacuo. The residue was triturated with sodium thiosulfate solution, filtered off, washed with water, dissolved in 300 ml. of acetone and the precipitated from the warm solution with 120 ml. of water. After cooling there is obtained 14.1 g. of 6α-fluoro-21-iodo-11β-hydroxy-17α-methyl-D-homo-1,4-pregnadien-3,20-dione. A total of 14.1 g. of the aforesaid 21-iodo compound was dissolved in 700 ml. of acetonitrile and heated for 3 hours under reflux with 14.1 ml. of ortho phosphoric acid and 42 ml. of triethylamine. Then the reaction solution was concentrated under reduced pressure, the residue taken up in methanol and the solution adjusted to pH 11 with 1N-methanolic sodium hydroxide solution. The residue was filtered off, the filtrate concentrated in vacuo and the residue taken up in 70 ml. of methanol. Addition of ether precipitated the disopdium salt. The disodium salt can be further purified by precipitation from methanol/ether. There is obtained 11.9 g. of disodium-(6α-fluoro-11β-hydroxy-3,20-dioxo-17α-methyl-D-homo-1,4-pregnadiene-21-yl) phosphate.

EXAMPLE 18

In the manner described in Example 8(e), 8(f) and 9, there was obtained from 3β-hydroxy-21-acetoxy-D-homo-5-pregnen-20-one the product 6α-fluoro-21-acetoxy-D-homo-4-pregnen-3,20-dione melting at 178°–180° C. which in turn following the procedure of Example 1(h) can be converted into 6α-fluoro-11β,21-dihydroxy-D-homo-4-pregnen-3,20-dione.

EXAMPLE 19 a. An Erlenmeyer flask containing 500 ml. of sterilized aqueous medium containing 0.3% yeast extract, 0.5% corn steep liquor and 0.2% starch, adjusted to pH 7, was inoculted with a lyophilized culture of Flavobacterium dehydrogenans (ATCC 139030) and shaken for 48 hours at 30° C. with 145 rotations per minute. A 20-liter fermentor containing 14.75 liters of the above mentioned growth medium was inoculated with 250 ml. of the bacteria suspension and was stirred for 24 hours at 29° C. with an air flow of 1650 liters per hour with 220 rotations per minute.

Out of this fermentation a total of 0.9 liters was placed in a 20 l. fermenter containing 15 l. of sterilized medium comprising the components described above.

The main fermentation then proceeded in the same manner as the pre-fermentation described above. The pH of the main fermentation was maintained between 6 to 7. After a period of 6 hours of incubation of total of 3.0 g. of 3β,21-diacetoxy-17α-methyl-D-homo-5-pregnen-20-one in 60 ml. of diemthyl formamide was added and fermented.

After a 32 hour contact time the fermentation mixture was extracted twice each with 15 l. of methylisobutyl ketone. The organic phase was concentrated, the residue taken up in methylene chloride, filtered through silica gel and then concentrated in vacuo. There was thus obtained 2.7 g. of 21-hydroxy-17α-methyl-D-homo-4-pregnen-3,20-dione as a crude product.

b. The above 21-hydroxy crude product was, without further purification, fermented in a manner analogous to Example 1(a) with Curvularia lunata and after workup in the predescribed manner there was obtained 480 mg. of 11β,21-dihydroxy-17α-methyl-D-homo-4-pregnen-3,20-dione melting at 198°–199.5° C.

EXAMPLE 20 a. Following the procedure of Example 1(h), a total of 3.0 g. of 6α-fluoro-21-acetoxy-17α-methyl-D-homo-4-pregnen-3,20-dione was fermented with *Aspergillus ochraceus* (ATCC 1008). After completion of the fermentation the broth was extracted with methylisobutyl ketone and the methylisobutyl ketone extract concentrated in vacuo to yield 6α-fluoro-11α,21-dihydroxy-17α-methyl-D-homo-4-pregnen-3,20-dione as a crude product.

b. The above crude product was then fermented in the manner of Example 2 with Bacillus lentus. Workup of the reaction mixture in the usual manner produced 890 mg. of 6α-fluoro-11α,21-dihydroxy-17a-methyl-D-homo-1,4-pregnadien-3,20-dione.

c. A total of 750 mg. of the above diene was treated in 10 ml. of dimethyl formamide with 2 ml. of acetic anhydride and 0.2 g. of lead diacetate and then stirred for 60 minutes at room temperature. The reaction mixture was diluted with methylene chloride, the methylene chloride phase washed with water and then taken to dryness.

d. The resulting crude 6α-fluoro-11α-hydroxy-21-acetoxy-17α-methyl-D-homo-1,4-pregnadien-3,20-dione was reacted with 7 ml. of pyridine and 0.8 ml. of methanesulfonyl chloride for 3 hours at 0° C. The reaction mixture was thrown into ice water, extracted with water, washed with methylene chloride and the methylene chloride phase was concentrated in vacuo. The resulting residue was dissolved in 10 ml of dimethyl formamide, treated with 0.8 g of lithium chloride and the mixture heated at 100° C for 90 minutes.

Thereafter the mixture was thrown into ice water, extracted with methylene chloride, the methylene chloride phase washed with water and then concentrated in vacuo. The resulting crude was purified chromotographically through a silica gel column, crystallized from methylene chloride-diisopropyl ether and yielded 210 mg. of 6α-fluoro-21-acetoxy-17α-methyl-D-homo-1,4,9(11)-pregnatrien-3,20-dione melting at 186°–188° C.

e. A total of 200 mg. of the above triene was then reacted in the manner of Example 5(b) with N-bromo succinimide so as to produce 180 mg. of 6α-fluoro-9α-bromo-11β-hydroxy-21-acetoxy-17α-methyl-D-homo-1,4-pregnadien-3,20-dione as a crude product.

f. The above bromohydrin was dissolved in 4 ml. of tetrahydrofuran, treated with 1.2 ml. of tributyl tin hydride and heated for 90 minutes at 80° C. A total of 1 mg. of azodiisobutyronitrile was added to the mixture and heating was continued for an additional 30 minutes. The reaction mixture was thrown into ice water, extracted with methylene chloride, the methylene chloride phase washed with 1N sulfuric acid, sodium bicarbonate solution and water, concentrated in vacuo so as to yield 110 mg. of 6α-fluoro-11β-hydroxy-21 acetoxy-17-αmethyl-D-homo-4-pregnen-3,20-dione.

EXAMPLE 21 a. A total of 5.6 g. of 3β-acetoxy-D-homo-5,17-pregnadien-20-one was treated with 350 ,l. of tetrahydrofuran and 6.8 g. of cupric bromide and then heated for 4 hours under reflux. The mixture was then thrown into ice water, extracted with methylene chloride, the methylene chloride phase washed, concentrated in vacuo and there was thus obtained 21-bromo-3β-aceotoxy-D-homo5,17-pregnadien-20-one as crude product, which after recrystallization from etherhexane melted at 155°–157° C.

b. In the manner of Example 1(d) the aforesaid bromo compound was reacted and worked up to yield 3β,21-diacetoxy-D-homo-5,17-pregnadien-20 -one melting at 133°–134° C.

c. The above obtained diacetate was then saponified in the manner of Example 1(e) so as to yield 3β,21-dihydroxy-D-homo-5,17-pregnadien-20-one.

d. The above obtained dihydroxy compound was esterified in the manner of Example 1(f) so as to obtain 3β-hydroxy-21-acetoxy-D-homo-5,17-pregnadien-20-one melting at 201°–202° C.

e. A solution containing 5.7 g. of the above 21-acetoxy compound was reacted with 170 ml. of toluene, 80 ml. of cyclohexanone and 6.6 g. of aluminumtert. butylate and was then heated for 2 hours on a water bath under reflux. The mixture was then thrown into ice water, acidified with hydrochloric acid and extracted with methylene chloride. The methylene chloride solution was washed with water, dried over sodium sulfate, concentrated in vacuo and the residue purified chromatographically over a silica gel column. There was thus obtained 21-acetoxy-D-homo-4,17-pregnadien-3,20-dione melting at 159°–160° C.

f. A solution of 3.0 g. of the above 21-acetoxy compound was dissolved in 300 ml. benzene and 30 ml. pyridine and then reacted with a solution containing 2.4 g. of osmium tetroxide in 60 ml. of benzene. The mixture was stirred for 2 hours at room temperature, dried in vacuo, the residue taken up in 400 ml. of dioxane, treated with 80 ml. of 40% sodium bisulfite solution and the mixture was the stirred for an additional 30 minutes. Then the mixture was concentrated to half volume in vacuo, the residue thrown into ice water, extracted with methylene chloride, the methylene chloride phase washed with sodium carbonate solution and water, dried over sodium sulfate and concentrated to dryness in vacuo. the residue was purified over a silica gel columne so as to yield 17α,17α-dihydroxy-21-acetoxy-D-homo-4-pregnen-3,20-dione melting at 230°–232° C. (from acetone).

g. The above dihydroxy compound was fermented in the manner of Example 1(b) with Curvularia lunata and after workup in the usual manner there was obtained 11β,17α,17aα,21-tetrahydroxy-D-homo-4-pregnen-3,20-dione melting at 261°–262° C.

EXAMPLE 22 a. 3β,11β-diacetoxy-androsta-3,5-dien-17-one was converted in a methylene chloride solution with ethylene glycol in the presence of orthoformic acid methyl ester and p-toluenesulfonic acid at room temperature into 3,11β-diacetoxy-17,17-ethylenedioxy-androsta-3,5-dione melting at 183°–186° C. This 17-ketal was then reduced in tetrahydrofuran-methanol by means of sodium borohydride to give 11β-acetoxy-17,17-ethylenedioxy-3β-hydroxy-androst-5-ene melting at 125°–126° C.

Cleavage of the ketal in aqueous with p-toluenesulfonic acid yielded 11β-acetoxy-3β-hydroxy-androst-5-en-17-one melting at 193°–195° C. This 17-keto steroid was the reacted with dimethylsulfoxonium-methylide in dimethyl formamide to give 21-nor-11β-acetoxy-17,20-epoxy-3β-hydroxy-pregn-5-ene melting at 155°–156° C.

The above epoxide was then converted utilizing alcohol and concentrated ammonia in an autoclave to 11β-acetoxy-17-aminomethyl-3β, 17-dihydroxy-androst-5-ene. After treatment with sodium nitrite in glacial acetic acid and water there was obtained D-homo-11β-acetoxy-3β-hydroxy-androst-5-en-17a-one melting at 230°–232° C.

Saponification of the above 11β-acetate in boiling methanolic potassium carbonate solution yielded D-homo-3β,11β-dihydroxy-androst-5-en 17a-one melting at 234°–236° C. This dihydroxy compound was then condensed with diethyl oxalate to yield 3β,11β-dihydroxy-17-ethoxalyl-D-homo-androst-5-en-17$^a$-one which in turn upon treatment with methylidide in acetone in the presence of potassium carbonate was converted to the 17-methyl derivative. After cleavage of the oxalyl group with methanolic sodium methylate solution there was obtained 3β,11β-dihydroxy-17β-methyl-D-homo-androst-5-17a-one melting at 209°–211° C.

The aforesaid dihydroxy compound was reacted in tetrahydrofuran with ethynyl magnesium bromide so as to yield 3β,11β,17βatrihydroxy-17β-methyl-17aβ-ethyneyl-D-homo-5-androstene, which after treatment with mercury-p-toluene sulfonic acid amide in boiling alcohol yielded 3β,11β,17aα-trihydroxy-17α-methyl-D-homo-5-pregnen-20-one melting at 212°–214° C.

b. A total of 1.7 g. of the above trihydroxy compound in 10 ml. of methanol was treated with 2.1 ml. of 10% methanolic calcium chloride solution and 1 g of anhydrous calcium oxide. A solution of 2.32 g of iodine and 600 mg of calcium chloride in 6 ml methanol was then added dropwise with strong stirring over a period of 30 minutes. Stirring was continued for an additional 10 minutes then the mixture thrown into ice water and extracted with methylene chloride. The extract was washed with dilute sodium chloride solution, dried and concentrated. There was then obtained 2.5 g of thin layer chromatographically uniform 3β, 11β-17aα-trihydroxy-21,21-diiodo-17α-methyl-D-homo-pregn-5-en-20-one which was utilized without further purification.

c. A total of 2.5g. of the above diiodide in 30 ml. of acetone was heated for 5 days under reflux with 0.3 ml. of acetic and and 3 g. of potassium acetate. The mixture was added to water and extracted with methylene chloride. The methylene chloride solution was washed with dilute sodium chloride solution, dried and concentrated. There is thus obtained 1.9 g. of 3β,11β,17aα-tirhydroxy-21-acetoxxy-17α-methyl-D-homo-pregn-5-en-20-one which was uniform on thin layer chromatography.

d. The above trihydroxy product was converted to 21-acetoxy-11β,17aα-dihydroxy-17α-methyl-D-homo-pregn-4-en-3,20-dione in the manner described in Example 1(g). The crude product after chromatography yielded pure final product melting at 210°–212° C. (from ethyl acetate).

EXAMPLE 23

A total of 2 g. of 3β,11β, 17aα-triydroxy-17α-methyl-D-homo-pregn-5-en-20-one in 20 ml. of cyclohexanone and 60 ml. of toluene was heated to boiling. A total of 10 ml. of solvent was distilled off. After cooling the mixture to about 5° C. a total of 2 g. of aluminum tritertiary butylate was added. The reaction mixture was then heated for one hour on a water bath. After allowing the mixture to cool it was added to dilute aqueous acetic acid and extracted with methylene chloride. The methylene chloride solution was washed with water, dried and concentrated. The difficultly volatile fraction was distilled off under high vacuum with a temperature of up to about 140° C. The residue was chromatographically purified. There was thus obtained 11β,17aα-dihydroxy-17α-methyl-D-homo-pregn-4-en-3,20-dione melting at 231°–234° C.

EXAMPLE 24 a. 3β,11α-dihydroxy-5-androsten-17-one was converted into 3β,11α-dihydroxy-17,20-epoxy-21-nor-5-pregnene melting at 190°–193° C. by utilizing dimethyl sulfoxonium methylide in dimethyl formamide.

The resulting epoxide was converted in an autoclave with alcohol and concentrated ammonia to 17-aminomethyl-3β,11α,17-trihydroxy-5-androstene, which upon treatement with sodium nitrite in dilute acetic acid provided 3β,11α-dihydroxy-D-homo-5-androsten-17a-one melting at 200°–201° C.

The above dihydroxy ketone was treated in liquid ammonia with potassium acetylide and there was thus obtained 3β,11α,17a-trihydroxy-17a-ethynyl-D-homo-5-androstene melting at 204°–205° C.

This ethynyl compound was esterified with acetic anhydride and pyridine at room temperature to yield 17a-hydroxy-3β,11α-diacetoxy-17a-ethynyl-D-homo-5-androstene melting at 208°–211° C.

The above diacetoxy compound was reacted in 2,4-lutidine with phosphorus oxychloride at 120° C for 20 hours to produce 3β,11α-diacetoxy-17a-ethynyl-D-homo-5,17-androstadiene as a colorless oil.

The above diene was reacted with mercury p-toluenesulfonic acid amide in aqueous ethanol to yield 3β,11α-diacetoxy-D-homo-5,17-pregnadien-20-one melting at 216°–217° C.

The resulting diacetate was reacted with sodium carbonate in methanol to produce 3β-hydroxy-11α-acetoxy-D-homo-5,17-pregnadien-20-one which melted at 220°–222° C. and upon Oppenauer oxidation yielded 11α-acetoxy-D-homo-4,17-pregnadien-3,20-dione melting at 147°–148° C.

The above dione was reacted in ether/pyridine with osmonium tetroxide to yield 17α,17aα-dihydroxy-11α-acetoxy-D-homo-4-pregnen-3,20-dione melting at 231°–232° C. which upon reaction with acetone in the presence of perchloric acid produced 11α-acetoxy-17α,17aα-isopropylidenedioxy-D-homo-4-pregnen-3,20-dione melting at 198°–200° C.

The above ester was saponified in methanolic solution with potassium hydroxide at room temperature to yield 11α-hydroxy-17α,17aα-isopropylidenedioxy-D-homo-4-pregnen-3,20-dione melting at 252°–258° C.

b. A solution containing 2.15 g. of the above hydroxy ketal and 2.2 ml. of methane sulfonylchloride in 20 ml. of pyridine was allowed to stand for 3 hours at 0° C. The reaction mixture was thrown into ice water and extracted with ethyl acetate. The organic extract was washed with dilute hydrochloric acid, water, sodium carbonate and again with water, dried over sodium sulfate and concentrated in vacuo to dryness. The residue was dissolved in 100 ml. of dimethyl formamide, and treated with 10 g. of lithium chloride and then heated at 100° C. for 90 minutes. It was then thrown into 500 ml. of ice water and extracted with methylene chloride. The extract was washed with dilute hydrochloric acid, water, sodium carbonate solution and water, dried over sodium sulfate and concentrated in vacuo. The residue was chromatographed over silica-gel. It was eluted with ether-hexane (1:1), the obtained fraction then purified by thin-layer chromatography and recrystallized from acetone-hexane. There was obtained pure 17α,17aα-isopropylidenedioxy-D-homo-pregna-4,9(11)-dien-3,20-dione melting at 150°–151° C.

c. Utilizing the procedure of Example 11(b) the above diene was reacted with N-chloro succinimide and perchloric acid to yield 9α-chloro-11β-hydroxy-17α,17aα-isopropylidenedioxy-D-homo-4-pregnen-3,20-dione.

EXAMPLE 25 a. A total of 800 mg. of 11β,21-dihydroxy-1,4-pregndien-3,20-dione was dissolved in 8 ml. of dimethylformamide, treated with 1.6 ml. of acetic anhydride and 112 mg. of lead diacetate and then stirred for 2 hours at room temperature. Then it was thrown into ice water, the product filtered, washed with water and dried. After recrystallization from acetone-hexane there was obtained 820 mg. of 21-acetoxy-11β-hydroxy-D-homo-1,4-pregnadien-3,20-dione melting at 192°–193° C.

b. A total of 760 mg. of the above dione in 4 ml. of dimethyl formamide and 0.76 ml. of pyridine was treated dropwise with 0.38 ml. of methanesulfonyl chloride. The mixture was stirred for 1½ hours at 80° C. Thereafter it was cooled to 20° C., thrown into ice water and the precipitate filtered off. The product was washed with water and dried in vacuo. After recrystallization from acetone-hexane there was obtained 650 mg. of 21-acetoxy-D-homo-1,4,9(11)-pregna-triene-3,20-dione melting at 135°–136° C.

c. A total of 374 mg. of the above triene was dissolved in 9 ml. of tetrahydrofuran and 535 mg. of N-bromosuccinimide. It was cooled to 0° C. and 3.3 ml. of 1N perchloric acid added dropwise. The mixture was stirred at 20° C for 30 minutes, thrown into ice cold sodium sulfide solution, the precipitate filtered off, dissolved in methylene chloride soluton, the methylene chloride solution was washed with water and concentrated in vacuo to yield 520 mg. of crude 21-acetoxy-9α-bromo-11β-hydroxy-D-homo-1,4-pregnadien-3,20-dione.

d. A total of 520 mg. of crude bromo compound was heated to reflux in 25 ml. of ethanol with 1.25 g. of potassium acetate for 1 hour. The reaction mixture was thrown into ice water, the precipitate filtered off, washed with water and dried in vacuo. After recrystallization from cyclohexane there was obtained 320 mg. of 21-acetoxy-9β,11β-epoxy-D-homo-1,4-pregnadien-3,20-dione melting at 152°–153° C.

EXAMPLE 26

A total of 700 mg. of 21-acetoxy-9α-fluoro-11β-hydroxy-D-homo-pregna-1,4-dien-3,20dione was saponfied by the procedure of Example 6 and worked up in similar manner. After recrystallization from acetone-hexane there was obtained 587 mg of 9α-fluoro-11β,21-dihydroxy-D-homo-pregna-1,4-dien-3,20-dione melting at 197°–199° C.

EXAMPLE 27

A total of 150 mg. of 21-acetoxy-D-homo-pregna-1,4,9(11)-trien-3,20-dione was dissolved at 0° C. in 1.5 ml. of dimethyl formamide and treated with 1.5 ml. of hydrochloric acid and 60 mg. of N-chlorosuccinamide. The mixture was stirred at 0° C. for 40 hours and was then thrown into ice cold potassium acetate solution. The precipitated product was filtered off and recrystallized from acetone-hexane. There was obtained 95 mg. of 9α-chloro-11β-fluoro-21-acetoxy-D-homo-1,4-pregnadien-3,20-dione melting at 169°–170° C.

EXAMPLE 28

A 2 l. Erlenmeyer flask containing 500 ml. of growth medium which had been sterilized in an autoclave for 30 minutes at 120° C. comprising 1% corn steep liquor, 1% soy powder and 0.005% soy oil and which is adjusted to a pH of 6.2 was inoculated with a lyophilized culture of Curvularia lunata (NRRL 2380) and was shaken on a rotation shaker for 72 hours at 30° C. This preliminary culture was then utilized to inoculate a total of 15 l. of medium in a 20 l. fermentor, said medium comprising 1% corn steep liquor, 0.5% glucose and 0.005% soy oil, having been adjusted to a pH of 6.2 and having been sterilized at 121° C and 1.1 atmospheres. The inoculate was germinated in the presence of Silicon SH as antifoaming agent at 29° C with an air flow of 10 l per minute at 1.7 atmospheres pressure and stirring at 220 rotations per minute for 24 hours. 1 l. of this culture broth was then introduced under sterile conditions into 14 l of a similarly sterilized medium comprising 1% corn steep liquor, 1.25% soy powder and 0.005% soy oil and the medium placed under the same conditions. After 6 hours a solution of 6 g of 21-acetoxy-D-homo-4-pregnen-3,20-dione in 300 ml of dimethylsufloxide was added.

After 44 hours of contact the fermentaion medium was stirred two times each with 10 l. of methylisobutyl ketone and the resulting extracts were concentrated in vacuo with a bath temperature of 50° C. The residue was washed clear of silicon oil with hexane and then was converted into a crystalline crude product (3.1 g.) by digestion with acetone/isopropyl ether which is then suitable in form for the following dehydration.

A sample of the crude product was recrystallized from acetone/ether to give 11β,21-dihydroxy-D-homo-4-pregnen-3,20-dione melting at 188°/191°–195° C.

EXAMPLE 29

A 2 l. Erlenmeyer flask containing 500 ml. of a growth medium sterilized for 30 minutes at 120° C. in an autoclave and comprising 1.5% peptone, 1.2% corn steep and 0.2% MgSO₄, after adjustment of the pH to 6.5 was inoculated with a lyophilized culture of Bacillus lentus (ATCC 13805). The mixture was shaken for 24 hours. This preliminary culture was then utilized to inoculate in a 20 l. fermentor a total of 15 l. of liquid growth medium which had been sterilized at 121° C. and 1.1 atmospheres comprising 0.2 yeast extract, 1% corn steep liquor and 0.1% glucose and the pH of the medium adjusted to 7.0. Then together with silicon SH as antifoaming agent it was germinated at 29° C. with aeration and stirring. After an incubation period of 6 hours a solution of 6 g. of 11β,21-dihydroxy-D-homo-4-pregnen-3,20-dione in 100 ml. of dimethyl formamide was added.

After 42 hours of contact the fermentation browth was extracted twice with 10 l. each of methylisobutyl ketone and the extracts concentrated in vacuo The residue was washed free of silicon oil with hexane and then after treatment with activated carbon in methanol it was recrystallized twice from acetone/ether to give 3 g. of 11β,21-dihydroxy-D-homo-1,4-pregnadien-3,20-dione melting at 170°/173°-174° C.

EXAMPLE 30

320 mg of 9β,11β-epoxy-21-acetoxy-D-homo-1,4-pregnadiene-3,20-dione is dissolved in 2 ml of dimethylformamide and added at −20° C to an solution of 2 ml dimethylformamide and 2 ml of hydrogen fluoride. The mixture is stirred at room temperature for 19 hours, than poured in on ice-cold solution of potassium acetate. The precipitated reaction product is filtered off with suction, recrystallised from aceton and 168,8 mg of 9α-fluoro-11β-hydroxy-21-acetoxy-D-homo-1,4-pregnadiene-3,20-dione are obtained. Melting point 227°-228° C.

EXAMPLE 31 a. 11β,17α-dihydroxy-21-acetoxy-D-homo-1,4-pregnadiene-3,20-dione is reacted with methanesulfochloride in sulfur dioxide to yield the 21-acetoxy-D-homo-1,4,9(11), 17-pregnatetraene-3,20-dione. Melting point 165°-166° C. The tetraene is reacted in dioxan with N-bromoacetamide and aqueous perchloric acid to yield the 9α-bromo-11β-hydroxy-21-acetoxy-D-homo-1,4,17-pregnatriene-3,20-dione. Melting point 193°-195° C. The bromohydrine is reacted in boiling ethanol with potassium acetate to yield the 9β,11β-epoxy-21-acetoxy-D-homo-1,4,17-pregnatriene-3,20-dione. Melting point 166°-167° C. The epoxide is reacted with hydrogen fluoride as described in Example 30 to yield the 9α-fluoro-11β-hydroxy-21-acetoxy-D-homo-1,4,17-pregnatriene-3,20-dione melting at 213°-214° C.

b. 1 g of 9α-fluoro-11β-hydroxy-21-acetoxy-D-homo-1,4-pregnatriene-3,20-dione is oxidised with 730 ml osmium tetroxide as described in Example 21 and 600 mg of 9α-fluoro-11β-17α,17aα-trihydroxy-21-acetoxy-D-homo-1,4-pregnadiene-3,20-dione are obtained. Melting point 265°-266° C.

EXAMPLE 32

500 mg of 9α-fluoro-11β-17α,17aα-trihydroxy-21-acetoxy-D-homo-1,4-pregnadiene-3,20-dione are dissolved in 25 ml of acetone, two drops of perchloric acid of 70% strength are added and the mixture is stirred at room temperature for 24 hours. Then 0,5 ml of saturated aqueous sodium bicarbonate solution are added, the mixture concentrated in vacuo, and the residue dissolved in methylene chloride. The methylene chloride solution is washed and concentrated and the residue is purified by chromatography over a column of silica gel. There are obtained after recrystallisation from acetone-hexane 160 mg 9α-fluoro-11β-hydroxy-17α,17aα-isopropylidenedioxy-21-acetoxy-D-homo-1,4-pregnadiene-3,20-dione which melts at 205°-207° C.

II. Pharamcological Formulations

EXAMPLE A

Composition for a salve:
| | |
|---|---|
| 0.01% | 6α-fluoro-11β-hydroxy-21-acetoxy-17α-methyl-D-homo-1,4-pregnadien-3,20-dione |
| 2.50% | Allercurhexachlorphenate, micronized particle size of about 8μ (Allercur = tradename for 1-p-chlorobenzyl-2-pyridine-methylbenz-imidazole) |
| 6.00% | Hostaphat KW 340 (the tertiary ester of O-phosphoric acid and fatty alcohol tetraglycol ether) |
| 0.10% | sorbic acid |
| 10.00% | neutral oil (Migloyol 812) |
| 3.50% | stearyl alcohol |
| 1.5% | wool fat, anhydrous DAB 6 |
| 76.39% | deionized water |

EXAMPLE B

Composition for a salve:
| | |
|---|---|
| 0.01 g. | 6α-fluoro-9α-chloro-11β-hydroxy-21-acetoxy-17α-methyl-D-homo-1,4-pregnadien-3,20-dione |
| 5.00 g. | white wax DAB 6 |
| 5.00 g. | wool fat anhydrous DAB 6 |
| 20.00 g. | Vaseline, white DAB 6 |
| 25.00 g. | Amphocerin K "Dehydag" |
| 14.97 g. | Paraffin oil, liquid DAB 6 |
| 30.00 g. | deionized water |
| 0.02 g. | Crematest perfume oil No. 6580 "Dragee" |

EXAMPLE C

Composition for eyedrops (oily)

100 mg. 6α-fluoro-11β-hydroxy-21-acetoxy-17α-methyl-D-homo-1,4-pregnadien-3,20-dione was dissolved in 100 ml. of ricin oil. The solution was filtered sterile together with 200 mg. of Chloramphenicol or another bacteriostatic agent and filled aseptically.

EXAMPLE D

Composition for ear drops 100 mg. of 6α-fluoro-11β-hydroxy-21-acetoxy-17α-methyl-D-homo-1,4-pregnadien-3,20-dione was dissolved in 100 ml of 1,2-propyleneglycol/ethyl alcohol (9:1). To the aforesaid solution there was added 200 mg of Chloramphenicol.

EXAMPLE E

Composition for a salve:
| | |
|---|---|
| 0.10 g. | sodium-(9α-fluoro-11β-hydroxy-3,20-dioxo-17α-methyl-D-homo-1,4-pregnadien-21-yl-sulfate |
| 45.00 g. | Vaseline (white) |
| 13.88 g. | Paraffin (viscous) |
| 6.00 g. | wax (white) |
| 5.00 g. | high molecular weight mixed esters from natural raw materials |
| 0.02 g. | perfume oil |
| 30.00 g. | water |

EXAMPLE F

Composition for a Cream:
| | |
|---|---|
| 0.10 g. | disodium-(6α-fluoro-11β-hydroxy-3,20-dioxo-17α-methyl-D-homo-1,4-pregnadien-21-yl)phosphate |

-continued

| | |
|---|---|
| 3.00 g. | polyoxyl stearate |
| 7.50 g. | Paraffin (viscous) |
| 7.50 g. | Vaseline (white) |
| 8.50 g. | glycerine-mono and distearate |
| 3.50 g. | stearyl alcohol |
| 0.07 g. | p-hydroxybenzoic acid methyl ester |
| 0.02 g. | perfume oil |
| 69.78 g. | water |

EXAMPLE G

Composition for a tablet:

| | |
|---|---|
| 0.250 mg. | 9α-fluoro-11β-hydroxy-21-hydroxy-D-homo-1,4-pregnadien-3,20-diene |
| 36.000 mg. | lactose DAB 6 |
| 75.780 mg. | corn starch USP XVI |
| 0.500 mg. | sodium lauryl sulfate (Texapon K 12) "Dehydag", USP XVI |
| 1.400 mg. | gelatin, white DAB 6 |
| 6.000 mg. | talcum DAB 6 |
| 0.024 mg. | Nipagin M (p-oxybenzoic acid methyl ester) DAB 6, 3. supplement |
| 0.011 mg. | Nipasol M (p-oxybenzoic acid propyl ester) DAB 6, 3. supplement |
| 0.035 mg. | Pistachio green dye "Dragoco" |

EXAMPLE H

| | |
|---|---|
| 0.025 mg. | 6α,9β-difluoro-11β-hydroxy-21-acetoxy-17α-methyl-D-homo-1,4-pregnadien-3,20-dione |
| 36.475 mg. | lactose DAB 6 |
| 75.530 mg. | corn starch, USP XVI |
| 0.500 mg. | sodium lauryl sulfate (Texapon K 12) "Dehydag", USP XVI |
| 1.400 mg. | gelatin, white DAB 6 |
| 6.00 mg. | talcum DAB 6 |
| 0.024 mg. | Nipagin M (p-oxybenzoic acid methyl ester) DAB 6 3. supplement |
| 0.035 mg. | pistachio green dye "Dragoco" |

EXAMPLE I

Preparation of injectable solution

A total of 50 mg. of 6α-fluoro-9α-chloro-11β-hydroxy-21-acetoxy-17α-methyl-D-homo-1,4-pregnadien-3,20-dione was dissolved in 10 ml. of sesame oil and the solution filled into 1 ml. ampuls which were then sterilized in the usual manner.

EXAMPLE J

Preparation of inhalation agent 1.000 of micronized 6α-fluoro-11β-hydroxy-16α-methyl-D-homo-1,4-pregnadien-3,20-dione (median particle size — less than 7μ) and 39.000 g. of ground lactose were mixed. Then 40 mg. of this mixture was filled into hard gelatin capsules.

The inhalation agent can, after opening of the capsule, be applied in a manner such as usually employed for treatment of a head cold or one may apply the inhalation agents utilizing a Spinhaler.

We claim:
1. A compound of the formula

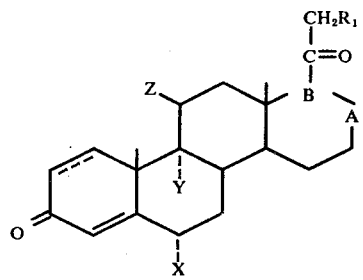

wherein — — — is a single bond or double bond in the 1,2-position, X is hydrogen, fluoro or methyl; Y is hydrogen or fluoro when Z is β-hydroxy or when Y is chloro, Z is β-hydroxy, β-fluoro or β-chloro; $R_1$ is hydrogen, fluoro, chloro, hydroxy, or hydroxy esterified with $C_{1-16}$ hydrocarbon carboxylic acid acyl, sulfate or phosphate and

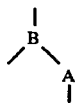

is a group selected from

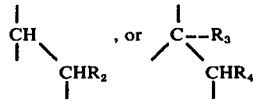

ps in which $R_2$ is hydrogen or methyl; $R_3$ is hydroxy or $C_{1-8}$ alkanoic acid acyloxy, and $R_4$ is methyl, hydroxy or $C_{1-8}$ alkanoic acid acyloxy provided that there is a double bond in the 1,2 position when X and $R_2$ or X and $R_4$ each independently are hydrogen or methyl.

2. A compound of claim 1 wherein X is hydrogen, Y is hydrogen and Z is β-hydroxy.

3. The compound of claim 2 which is 11β,21-dihydroxy-17α-methyl-D-homo-1,4-pregnadien-3,20-dione.

4. The compound of claim 2 which is 11β-hydroxy-21-butyryloxy-17α-methyl-D-homo-1,4-pregnadien-3,20-dione.

5. The compound of claim 2 which is 11β-hydroxy-21-acetoxy-17α-methyl-D-homo-1,4-pregnadien-3,20-dione.

6. The compound of claim 2 which is 11β-hydroxy-21-acetoxy-D-homo-1,4-pregnadien-3,20-dione.

7. The compound of claim 2 which is 11β,21-dihydroxy-D-homo-1,4-pregnadien-3,20-dione.

8. A compound of claim 1 wherein X is fluoro, Y is hydrogen an Z is β-hydroxy.

9. The compound of claim 8 which is 6α-fluoro-11β,21-dihydroxy-17α-methyl-D-homo-4-pregnen-3,20-dione.

10. The compound of claim 8 which is 6α-fluoro-11β,21-dihydroxy-17α-methyl-D-homo-1,4-pregnadien-3,20-dione.

11. The compound of claim 8 which is 6α-fluoro-11β-hydroxy-21-acetoxy-17α-methyl-D-homo-1,4-pregnadien-3,20-dione.

12. The compound of claim 8 which is 6α-fluoro-11β,21-dihydroxy-D-homo-4-pregnen-3,20-dione.

13. The compound of claim 8 which is 6α-fluoro-11β-hydroxy-21-acetoxy-17α-methyl-D-homo-4-pregnen-3,20-dione.

14. A compound of claim 1 wherein X is hydrogen, Y is fluoro and Z is βhydroxy.

15. The compound of claim 14 which is 9α-fluoro-11β-hydroxy-21-acetoxy-17α-methyl-D-homo-1,4-pregnadien-3,20-dione.

16. The compound of claim 14 which is 9α-fluoro-11β,21-dihydroxy-17α-methyl-D-homo-1,4-pregnadien-3,20-dione.

17. The compound of claim 14 which is 9α-fluoro-11β-hydroxy-21-acetoxy-D-homo-1,4-pregnadien-3,20-dione.

18. The compound of claim 14 which is 9α-fluoro-11β,21-dihydroxy-D-homo-1,4-pregnadien-3,20-dione.

19. A compound of claim 1 wherein X is fluoro, Y is chloro and Z is β-hydroxy.

20. The compound of claim 19 which is 6α-fluoro-9α-chloro-11β-hydroxy-21-trimethylacetoxy-17α-methyl-D-homo-1,4-pregnadien-3,20-dione.

21. The compound of claim 19 which is 6α-fluoro-9α-chloro-11β-hydroxy-21-acetoxy-17α-methyl-D-homo-1,4-pregnadien-3,20-dione.

22. A compound of claim 1 wherein X is fluoro, Y is fluoro and Z is β-hydroxy.

23. The compound of claim 22 which is 6α,9α-difluoro-11β-hydroxy-21-acetoxy-17α-methyl-D-homo-1,4-pregnadien-3,20dione.

24. The compound of claim 22 which is 6α,9α-difluoro-11β,21-dihydroxy-17α-methyl-D-homo-1,4-pregnadien-3,20-dione.

25. A compound of claim 1 wherein X is fluoro, Y is chloro and Z is chloro.

26. The compound of claim 25 which is 6α-fluoro-9α,11β-dichloro-21-acetoxy-17α-methyl-D-homo-1,4-pregnadien-3,20-dione.

27. A compound of claim 1 wherein X is fluoro, Y is chloro and Z is fluoro.

28. The compound of claim 27 which is 6α,11β-difluoro-9α-chloro-21-acetoxy-17α-methyl-D-homo-1,4-pregnadien-3,20-dione.

29. A compound of claim 1 wherein X is hydrogen, Y is chloro and Z is β-hydroxy.

30. A compound of claim 1 wherein X is hydrogen, Y is chloro and Z is fluoro.

31. The compound of claim 30 which is 9α-chloro-11β-fluoro-21-acetoxy-D-homo-1,4-pregnadien-3,20-dione.

* * * * *